(12) United States Patent
Forssmann et al.

(10) Patent No.: US 7,741,287 B2
(45) Date of Patent: Jun. 22, 2010

(54) PEPTIDES FOR THE TREATMENT OF HERPES VIRUS INFECTIONS

(75) Inventors: Wolf-Georg Forssmann, Hannover (DE); Frank Kirchhoff, Ulm (DE); Jan Münch, Ulm (DE); Ludger Ständker, Hannover (DE)

(73) Assignee: IPF PharmaCeuticals GmbH, Hannover (DE)

( * ) Notice: Subject to any disclaimer, the term of this patent is extended or adjusted under 35 U.S.C. 154(b) by 531 days.

(21) Appl. No.: 11/658,269

(22) PCT Filed: Aug. 16, 2005

(86) PCT No.: PCT/EP2005/054028

§ 371 (c)(1),
(2), (4) Date: Jan. 24, 2007

(87) PCT Pub. No.: WO2006/018431

PCT Pub. Date: Feb. 23, 2006

(65) Prior Publication Data

US 2008/0312144 A1 Dec. 18, 2008

Related U.S. Application Data

(60) Provisional application No. 60/602,313, filed on Aug. 18, 2004.

(30) Foreign Application Priority Data

Aug. 18, 2004 (EP) .................................. 04019552

(51) Int. Cl.
*A61K 38/17* (2006.01)
(52) U.S. Cl. ........................................................ 514/12
(58) Field of Classification Search ................... 514/12, 514/14; 530/324, 327, 333, 344, 345, 402
See application file for complete search history.

(56) References Cited

U.S. PATENT DOCUMENTS

| | | | | |
|---|---|---|---|---|
| 5,861,483 | A * | 1/1999 | Wolpe | 530/385 |
| 5,922,854 | A * | 7/1999 | Kumar et al. | 536/23.5 |
| 6,022,848 | A * | 2/2000 | Kozlov et al. | 514/6 |
| 6,171,826 | B1 * | 1/2001 | Levine et al. | 435/69.6 |
| 6,337,314 | B1 * | 1/2002 | Hoffman et al. | 514/2 |
| 2003/0104984 | A1 * | 6/2003 | Tsyrlova et al. | 514/6 |

FOREIGN PATENT DOCUMENTS

| | | |
|---|---|---|
| EP | 1 481 988 A | 12/2004 |
| GB | 2 382 347 A | 5/2003 |
| JP | 01 009997 A | 1/1989 |
| WO | WO 01/94386 A | 12/2001 |

* cited by examiner

*Primary Examiner*—Andrew D Kosar
(74) *Attorney, Agent, or Firm*—Venable LLP; Ann S. Hobbs

(57) ABSTRACT

The present invention relates to the use of a peptide having the amino acid sequence $NH_2$-VCVLAHHFGKEFTP-PVQAAYQKVVAGVANALAHKYH-COOH (SEQ ID NO:1) as well as variants, derivatives and fragments of the peptide for the treatment of viral diseases.

6 Claims, 2 Drawing Sheets

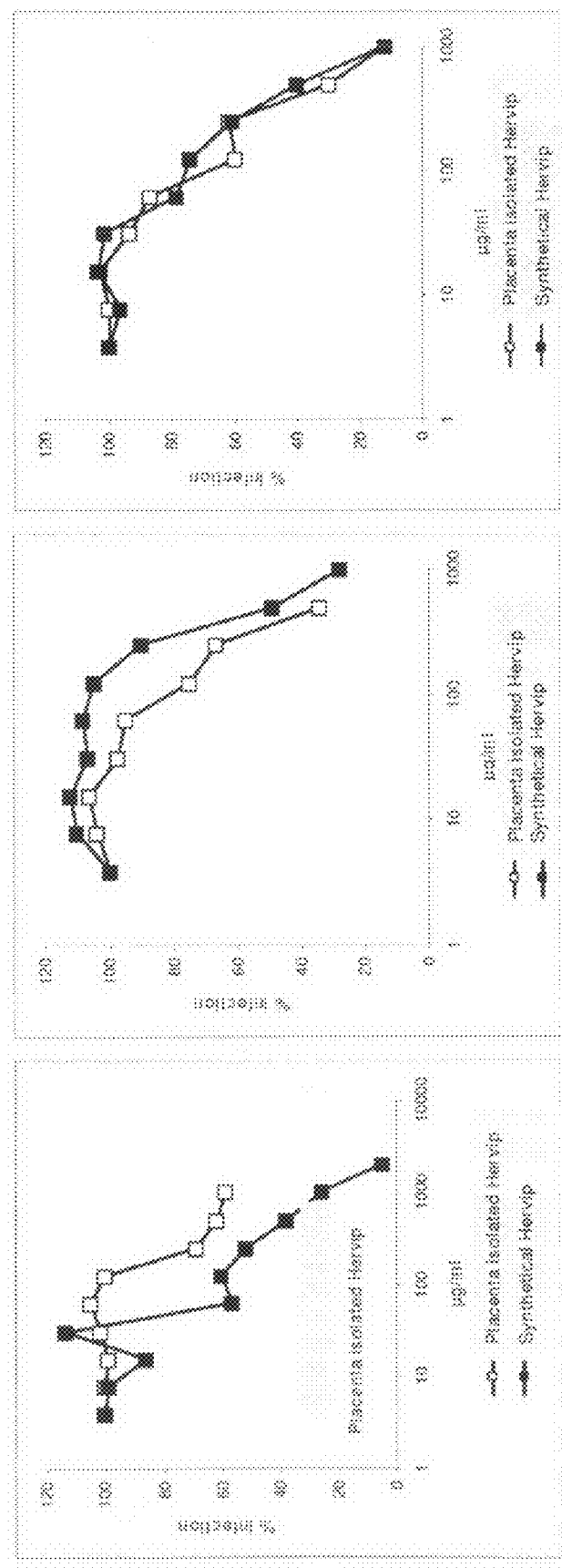

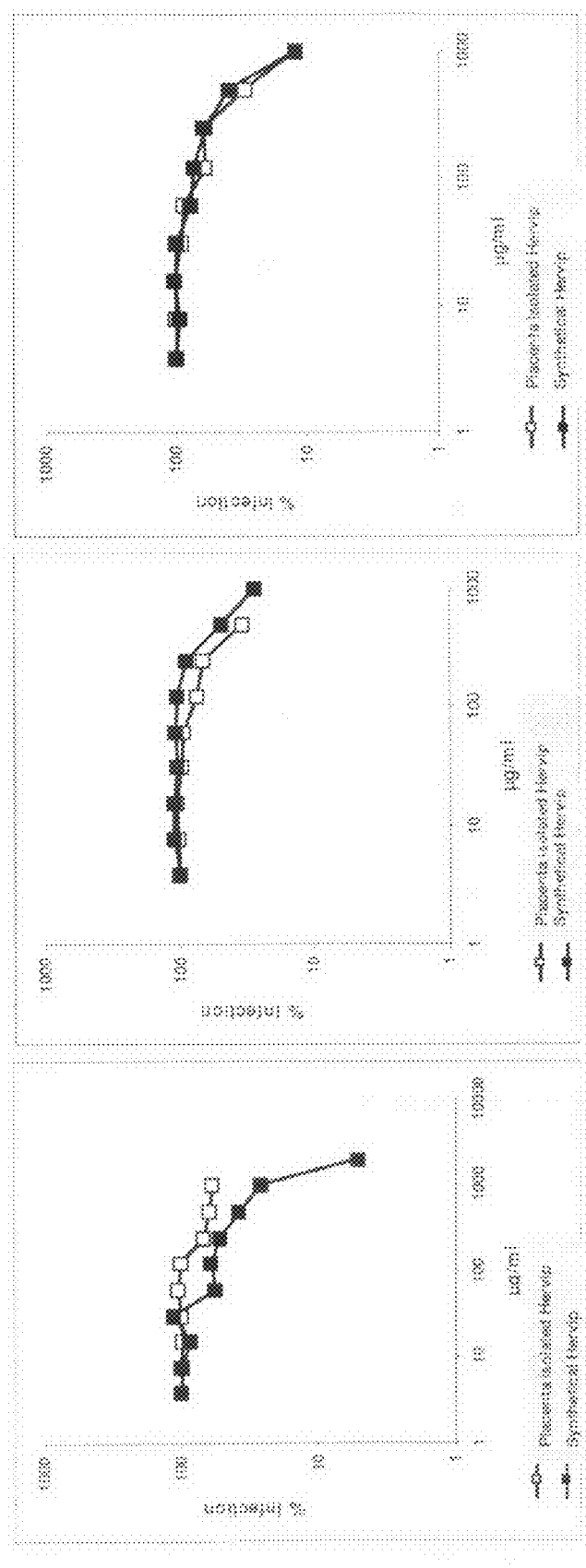

PEPTIDES FOR THE TREATMENT OF HERPES VIRUS INFECTIONS

CROSS-REFERENCE TO RELATED APPLICATIONS

This application is the U.S. national phase of International Appl. No. PCT/EP2005/054028, filed Aug. 16, 2005, which published under PCT Article 21(2) in English; said PCT/EP2005/054028 claims the benefit of European Appl. No. 04019552.1, filed Aug. 18, 2004 and also claims the benefit of U.S. Provisional Appl. No. 60/602,313, filed Aug. 18, 2004.

BACKGROUND OF THE INVENTION

1. Field of the Invention

The present invention relates to the use of a peptide having the SEQ ID No. 1 for the treatment of viral diseases.

2. Background Information

While a number of effective antibiotics are available for the treatment of diseases caused by bacteria, the treatment of viral diseases is often difficult. In many cases, only vaccination methods if at all, but no effective therapeutic agents are available. The provision of therapeutically active substances which can be administered after a viral infection is of great importance.

Diseases caused by herpes simplex viruses are among the most frequent infectious diseases of the skin. Most infections occur in the face and in the genital region. The disease is caused by an infection with herpes simplex viruses. Frequent variants thereof are herpes simplex virus type 2 (HSV-2) and herpes simplex virus type 1 (HSV-1). HSV-2 is commonly associated with herpes genitalis and HSV-1 commonly with herpes labialis.

Most people become infected with the herpes virus already in their childhood. When herpes breaks out in the adult age, a renewed infection from another person may have occurred, or activation of the "silent" viruses present in one's own body. The first herpes infection mostly involves the formation of small blisters in the oral cavity (gingivostomatitis). If the vagina is afflicted, the infection is called vulvovaginitis, and in the urethra, it is called urethritis. A second or later disease results in herpes labialis (cold sore). A particularly severe form of herpes infection (eczema herpeticatum) may occur in people suffering from neurodermitis.

An overcome episode of herpes infection does not cause immunity. In most cases, there are frequent recurrences of the disease. A satisfactory therapy of herpes infection has not been known to date. Also, to date, no possibility has been found for destroying the virus resting in the body. For this reason, symptoms, such as pain, if any, fever and the inflammations, are treated in a herpes infection. Ointments comprising antivirally active ingredients, such as aciclovir, only shorten the duration of the disease. However, they only have limited influence on the symptomatic course of a herpes infection.

DESCRIPTION OF THE INVENTION

The object of the invention is to provide an active substance effective against viral diseases, especially herpes. In particular, the active substance is to act directly against the virus and the viral infection rather than merely alleviating symptoms or acting against collateral phenomena, for example, accompanying microbial colonizations.

The object of the invention is surprisingly achieved by the use of a peptide having the sequence SEQ ID No. 1 for antiviral treatment according to any of claims 1 to 6. In the following, the peptide is referred to as Hervip.

The peptide itself has already been known. It was isolated from human placenta by means of a bacterial radial diffusion inhibition test (Liepke et al., 2003; WO 01/94386). Hervip comprises amino acids 112-147 of human β-hemoglobin.

It may be obtained by the methods described from human placenta extract and characterized biochemically by mass spectrometry (electrospray method; ESI-MS) and N-terminal sequencing (Edman degradation). The determination of the molecular weight by means of electrospray mass spectrometry yields a molecular weight of 3902 Da.

It has been found that this peptide has a very specific antiviral activity, especially against HSV-2 and HSV-1, in addition to an already known antimicrobial activity. This finding is surprising because (herpes) viruses differ significantly in their structure and mechanism of action from microbes, such as funghi or bacteria. Thus, unlike bacteria, (herpes) viruses use specific molecular structures on their surface and on the surface of their target cells for cellular entry and infection, and they proliferate by using the cellular transcription and translation apparatus of their target cells.

Antibacterial peptides predominantly act through incorporation into bacterial membranes, which causes permeabilization of such membranes and thus death of the microorganisms [Vaara et al., 1992]. In this respect, the mechanisms of action of previously described antimicrobially active substances are basically different from those of antiviral inhibitors, because the latter attack quite different molecular structures which are necessary for the infection or replication.

Hervip is a peptide with an amino acid sequence from the β-chain of human hemoglobin corresponding to the sequence region 112-147 of human β-hemoglobin (accession No.: 4378804). The peptide with this sequence region unexpectedly has a specific antiviral activity. The precursor protein of Hervip, which is human hemoglobin, consists of two different protein chains, the α and β chains, and in addition to its fundamentally important task as an oxygen carrier in the organism, it also has a function as a parent molecule for bioactive hemoglobin fragments derived from its sequence [Ivanov et al., 1997]. Surprisingly, these fragments are not associated any more with the actual oxygen carrier function of hemoglobin, but serve quite different biological functions. Thus, hemoglobin fragments which are derived from both the α and β chains have been identified to have, for example, a growth-factor releasing [Schally 1971], analgetic [Takagi et al., 1979; Fukui et al., 1983] or also opioid-like [Brantl et al., 1986] effect.

Most recently, hemoglobin fragments have also been discovered which have an antimicrobial activity, for example, a bovine hemoglobin fragment of the α chain isolated from a tick [Fogaca et al., 1999].

The peptide Hervip as purified from placenta and also the synthetically prepared Hervip exhibit a dose-dependent effectiveness against HSV-2 cultured in vitro.

The substance Hervip according to the invention may be employed for inhibiting the replication, transmission and infection of herpes viruses in a therapy of viral infectious diseases. A therapeutical application is indicated, in particular, for topical application with infections of the skin and mucosae, also in the genital region, above all. However, systemic administration for the therapy of infectious diseases caused by herpes viruses is also possible.

The use of Hervip according to the invention comprises the treatment of diseases caused by infection with herpes viruses.

According to the invention, Hervip has an immediate direct antiviral effect rather than a merely indirect effect against an accompanying microbial miscolonization. Preferably, those viral diseases which are not accompanied by a substantial microbial miscolonization by bacteria, fungi etc. are treated.

Also suitable for the described antiviral treatment according to the invention are derivatives, variants and fragments of Hervip. The derivatives, variants and fragments are obtainable by routine methods of amino acid deletion, substitution and insertion. Particularly suitable are amidated, acetylated, sulfated, phosphorylated, glycosylated, oxidized or polyethylene glycol-modified derivatives.

Preferred embodiments relate to variants and fragments obtained by conservative exchange, insertion and/or deletions of amino acids, and/or variants which contain from 1 to 10, especially from 1 to 5 or 1, 2 or 3 additional amino acids at the N and/or C termini of the peptide.

It was found that a fragment of Hervip truncated at the C-terminus and consisting of the first 12 amino acids only shows high activity in a cellular infection assay. Therefore, in a preferred embodiment the fragments of Hervip comprise at least 12 N-terminal amino acids. In another preferred embodiment, the fragments of Hervip lack the N-terminal amino acid valine.

The derivatives, fragments and variants have at least 80%, especially 90%, preferably 95% sequence identity with Hervip and are antivirally effective.

Preferably, their antiviral activity is at least as strong as that of Hervip, but it may also be lower and should be at least 10%, 25% or 50% of the antiviral activity of Hervip. Such antiviral activity is preferably established in a hydrogenase/formazane assay or as described in the Example.

The use is preferably effected in suitable galenic formulations, preferably formulated for infusions, as ointments, tablets, sprays, "slow release" capsules and similar preparations, and/or in combination with other antiviral therapeutic agents.

The invention is further illustrated by means of the following Examples:

EXAMPLES

For the isolation of Hervip, enrichment and fractioning of a placenta peptide extract was effected by means of cation-exchange and reverse-phase chromatography according to the known method (Liepke et al., 2003; WO 01/94386). Corresponding fractions were examined for inhibition of HSV-2 (see below in "Determination of the biological activity of Hervip"). The active peptide was isolated and characterized as a fragment of the β chain of human hemoglobin, amino acids 112-147 (accession No. 4378804):

(i) The theoretical mass of the protein fragment hemoglobin molecular β chain, amino acids 112-147, of 3902.5 is identical with the measured mass of 3902.5 Da.

(ii) In addition, a chemical synthesis of the Hervip sequence was performed by known methods followed by a verification by determining the molecular mass and sequence. Synthetic Hervip has identical properties upon chromatographic analysis compared to the native peptide.

The fragment of the β chain of human hemoglobin, amino acids 112-147 (accession No. 4378804) is referred to herein as Hervip (herpes virus inhibitory peptide).

Determination of the Biological Activity of Hervip

The infection rate of herpes simplex virus is determined by means of a cellular assay. Inhibitors of HSV-2 reduce the infection rate in this assay.

1000 ELVIS cells (Diagnostic Hybrids, USA) in 100 µl of cell culture medium were sown in a reaction space of a 96-well cell culture plate. ELVIS cells are a genetically modified baby hamster kidney (BHK) cell line whose genome stably contains the E. coli lacZ gene under the control of the inducible HSV promoter ICP6. After successful infection by HSV-1 or HSV-2, the viral ribonucleotide reductase ICP6 is expressed, which subsequently induces the expression of the lacZ gene through the ICP6 promoter. After 24 h from the sowing, chromatographic fractions, purified or synthetic peptide were dissolved in cell culture medium and added to the cells in a volume of 50 µl. Two hours after the incubation of the cells with the samples at 37° C., the infection was effected with 50 µl of HSV-2 or HSV-1 (total volume 200 µl). Depending on the experimental approach, a different MOI (multiplicity of infection) of from 0.01 to 10 was used for the infection. The HSV replication was detected 2 days after the infection by detecting the lacZ-encoded β-galactosidase in a Gal-Screen Chemiluminescence Reporter Kit (Tropix, # ABGS100M).

The dose-dependent inhibitory activity of isolated and synthetically prepared Hervip against HSV-1 and HSV-2 is shown in FIGS. 1 and 2.

IC50 values obtained were 300-400 µg/ml for native and synthetic Hervip. A synthetic Hervip peptide lacking the N-terminal valine residue had a corresponding antiviral activity. A synthetic N-terminal Hervip fragment having the sequence VCVLAHHFGKEF (SEQ ID NO:2) had an IC50 value in the range of 68-200 µg/ml.

BRIEF DESCRIPTION OF THE DRAWINGS

Figures:

FIGS. 1a and 2a: Antiviral activity of Hervip purified from placenta and synthetic Hervip on HSV-2. One day after the sowing, 1000 ELVIS cells were incubated with the stated amounts of Hervip for 2 h and subsequently infected with HSV-2. Two days after the infection, the HSV-2 infection was detected by detecting β-galactosidase. The mean values from 6 independent experiments performed in triplicate with a total of 3 different clinical HSV-2s are shown. The data is shown in half-logarithmic plots FIGS. 1a, b, c and in logarithmic plots in FIGS. 2a, b, c.

FIGS. 1b and 2b: Dose-effect curve of Hervip isolated from placenta and synthetic Hervip on HSV-2 (isolate Erlangen Diagnostik 2000). The mean values from one experiment performed in triplicate are shown. For a description of the experiment, see FIG. 1a/2a.

FIGS. 1c and 2c: Dose-effect curve of Hervip isolated from placenta and synthetic Hervip on HSV-1 (isolate Erlangen Diagnostik 2000). The mean values from 3 experiments performed in duplicate or triplicate are shown. For a description of the experiment, see FIG. 1a/2a.

REFERENCES

Ivanov V T, Karelin A A, Philippova M M, Nazimov I V, Pletnev V Z. Hemoglobin as a source of endogenous bioactive peptides: the concept of tissue-specific peptide pool. Biopolymers. 1997; 43(2):171-88.

Schally A V, Baba Y, Nair R M, Bennett C D. The amino acid sequence of a peptide with growth hormone-releasing activity isolated from porcine hypothalamus. J Biol Chem. 1971 November; 246(21):6647-50.

Takagi H, Shiomi H, Ueda H, Amano H. A novel analgesic dipeptide from bovine brain is a possible Met-enkephalin releaser. Nature. 1979 Nov. 22; 282(5737):410-2.

Fukui K, Shiomi H, Takagi H, Hayashi K, Kiso Y, Kitagawa K. Isolation from bovine brain of a novel analgesic pentapeptide, neo-kyotorphin, containing the Tyr-Arg (kyotorphin) unit. Neuropharmacology. 1983 February; 22(2): 191-6.

Brantl V, Gramsch C, Lottspeich F, Mertz R, Jaeger K H, Herz A. Novel opioid peptides derived from hemoglobin: hemorphins. Eur J Pharmacol. 1986 Jun. 17; 125(2): 309-10.

Fogaca A C, da Silva P I Jr, Miranda M T, Bianchi A G, Miranda A, Ribolla P E, Daffre S. Antimicrobial activity of a bovine hemoglobin fragment in the tick Boophilus microplus. J Biol Chem. 1999 Sep. 3; 274(36):25330-4.

Liepke C, Baxmann S, Heine C, Breithaupt N, Standker L, Forssmann W G. Human hemoglobin-derived peptides exhibit antimicrobial activity: a class of host defense peptides. J Chromatogr B Analyt Technol Biomed Life Sci. 2003 Jul. 5; 791(1-2):345-56.

Vaara M. Agents that increase the permeability of the outer membrane. Microbiol Rev. 1992 September; 56(3):395-411.

What is claimed is:

1. A method for treating viral disease comprising:
   administering to a subject in need thereof an effective amount of a peptide consisting of the amino acid sequence SEQ ID NO:1, or an amidated, acetylated, sulfated, phosphorylated, glycosylated, oxidized or polyethylene glycol-modified derivative thereof, wherein said derivative has inhibitory activity against HSV-2 in a cellular infection assay.

2. The method of claim 1, wherein said viral disease is herpes.

3. The method of claim 1, wherein said viral disease has been caused by infection with herpes simplex virus.

4. The method of claim 1, wherein said viral disease does not cause a microbial miscolonization.

5. The method of claim 1, wherein said peptide is formulated in galenic formulations for infusions, ointments, tablets, sprays, slow release capsules and similar preparations.

6. The method of claim 5, wherein said galenic formulation further comprises other antiviral therapeutic agents.

* * * * *

SEQUENCE LISTING

```
<160> NUMBER OF SEQ ID NOS: 3

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence:Hervip
      peptide

<400> SEQUENCE: 1

Val Cys Val Leu Ala His His Phe Gly Lys Glu Phe Thr Pro Pro Val
 1               5                  10                  15

Gln Ala Ala Tyr Gln Lys Val Val Ala Gly Val Ala Asn Ala Leu Ala
            20                  25                  30

His Lys Tyr His
        35

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence:fragment of
      Hervip peptide

<400> SEQUENCE: 2

Val Cys Val Leu Ala His His Phe Gly Lys Glu Phe
 1               5                  10

<210> SEQ ID NO 3
<211> LENGTH: 35
<212> TYPE: PRT
<213> ORGANISM: Artificial Sequence
<220> FEATURE:
<223> OTHER INFORMATION: Description of Artificial Sequence:fragment of
      Hervip peptide

<400> SEQUENCE: 3

Cys Val Leu Ala His His Phe Gly Lys Glu Phe Thr Pro Pro Val Gln
 1               5                  10                  15

Ala Ala Tyr Gln Lys Val Val Ala Gly Val Ala Asn Ala Leu Ala His
            20                  25                  30

Lys Tyr His
        35
```